United States Patent [19]

Sitzmann

[11] Patent Number: 5,025,102

[45] Date of Patent: Jun. 18, 1991

[54] BIS(2-FLUORO-2,2-DINITROETHYL)CARBONATE PENTAFLUOROSULFANYLIMINE

[75] Inventor: Michael E. Sitzmann, Adelphi, Md.

[73] Assignee: The United States of America as represented by the Secretary of the Navy, Washington, D.C.

[21] Appl. No.: 553,835

[22] Filed: Jul. 18, 1990

[51] Int. Cl.$^5$ ............................................. C07C 257/06
[52] U.S. Cl. ....................................................... 558/6
[58] Field of Search ............................................ 558/6

Primary Examiner—Mary C. Lee
Assistant Examiner—Joseph K. McKane
Attorney, Agent, or Firm—Kenneth E. Walden; Roger D. Johnson

[57] ABSTRACT $SF_5N=C[OCH_2CF(NO_2)_2]_2$, which is useful as an energetic plasticizer in plastic bonded explosives.

1 Claim, No Drawings

BIS(2-FLUORO-2,2-DINITROETHYL)CARBONATE PENTAFLUOROSULFANYLIMINE

BACKGROUND OF THE INVENTION

The invention relates to explosives and more particularly to energetic plasticizers for plastic bonded explosives.

Bis(2-fluoro-2,2-dinitroethyl)formal, $CH_2[OCH_2CF(NO_2)_2]_2$ (FEFO), has the highest density (1.60 g/cc) of any energetic plasticizer currently in use. For energetic materials, density is a critical property since the performance of the material is proportional to the square of its density. Hence, an energetic plasticizer with a significantly higher density than FEFO would offer a definite advantage. Also an energetic plasticizer with a lower melting point than that of FEFO (mp of FEFO is 14° C.) is preferable especially if the lower melting melting point is not accompanied by the usual higher volatility. Even with its relatively high melting point, FEFO suffers a disadvantage in that it has higher volatility than desired In addition, FEFO has a limitation in that it does not contain sufficient oxidant oxygen and fluorine) to combust all carbon and hydrogen to $CO_2$ $H_2O$, and HF. For this reason, an energetic plasticizer with higher oxidant level than FEFO is preferable for use in explosive formulations (essentially all explosive formulations are fuel rich and extra oxidant will produce additional energy.) Thus, it would be highly desirable to have available an energetic plasticizer that provides a combination of high density, high oxidant level, low melting point, and low volatility.

SUMMARY OF THE INVENTION

Accordingly an object of this invention is to provide a new energetic plasticizer for plastic bonded explosives.

Another object of this invention is to provide a new energetic plasticizer having a high density.

A further object of this invention is to provide a new energetic plasticizer having a low melting point and low vapor pressure.

Yet another object of this invention is to provide a new energetic plasticizer having a high oxidant level.

These and other objects of this invention are accomplished by providing bis(2-fluoro-2,2-dinitroethyl)carbonate, pentafluorosulfanylimine and a method of preparing it.

DETAILED DESCRIPTION OF THE PREFERRED EMBODIMENT

Bis(2-fluoro-2,2-dinitroethyl)carbonate, pentafluorosulfanylimine, $SF_5N=C[OCH_2CF(NO_2)_2]_2$, is useful as a high energy plasticizer for high performance plastic bonded explosives. The performance of energetic explosive materials is proportional to the square of the density of the material. The density of $SF_5N=C[OCH_2CF(NO_2)_2]_2$ is 1.82 g/cm$^3$. Previously, bis(2-fluoro-2,2-dinitroethyl)formal (FEFO), $H_2C[OCH_2CF(NO_2)_2]_2$ was the densest high energy plasticizer (1.60 g/cm$^3$). Further, the melting point ($-4°$ C.) of $SF_5N=C[OCH\ CF(NO_2)_2]_2$ is much lower than that of FEFO (14° C.). Moreover, the volatility of $SF_5N=C[OCH_2CF(NO_2)_2]_2$ (0.0536% wt. loss per minute at 117° C.) was about one-half that of FEFO (0.1039% wt loss per minute at 117° C.). Finally, the $SF_5$ group is capable of oxidizing carbon and hydrogen atoms into COS, $H_2S$, and HF. This results in $SF_5N=C[OCH_2CF(NO_2)_2]_2$ having a higher oxidant content than FEFO. All of these advantages favor the replacement of FEFO with bis(2-fluoro-2,2-dinitroethyl)carbonate, pentafluorosulfanylimine, $SF_5N=C[OCH_2CF(NO_2)_2]_2$.

The bis(2-fluoro-2,2-dinitroethyl)carbonate, pentafluorosulfanylimine is produced by reacting two moles of 2-fluoro-2,2-dinitroethanol with each mole of pentafluorosulfanyldichloroimine in the presence of a proton aceptor (base) such as pyridine at a temperature of preferably from about $-5°$ C. to about 5° C. and more preferably from 0° C. to 3° C.:

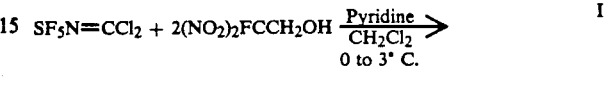

$$SF_5N=CCl_2 + 2(NO_2)_2FCCH_2OH \xrightarrow[\text{0 to 3° C.}]{\text{Pyridine}} \quad I$$

$$SF_5N=C[OCH_2CF(NO)_2)_2]_2.$$

A slight excess of 2-fluoro-2,2-dinitroethanol is preferably used to insure that the bis(2-fluoro-2,2-dinitroethyl)carbonate, pentafluorosulfanylimine is produced.

The reaction is preferably run in a suitable solvent which is chemically inert to the reactants, product, and proton acceptor and in which the reactants are soluble. Preferred solvents include dichloromethane, chloroform, 1,2-dichloroethane,,1,1-dichloroethane, 1,1,2-trichloroethane, 1,1,1-trichloroethane, and mixtures thereof, with dichloromethane being the most preferred solvent Preferred proton aceptors include tertiary amines which will not chemically react with the starting materials. Of the tertiary amine proton aceptors, pyridine and triethylamine are more preferred, with pyridine being the most preferred.

To more clearly illustrate this invention, the following example is presented. It should be understood, however, that this example is presented merely as a means of illustration and are not intended to limit the scope of the invention in any way.

EXAMPLE

Bis(2-fluoro-2-2-dinitroethyl)carbonate, pentafluorosulfanylimine

A solution of 2.6 g (0.017 mole) of 2-fluoro-2,2-dinitroethanol and 1.6 g (0.007 mole) of pentafluorosulfanyldichloroimine in 7 mL of dry dichloromethane was stirred in an ice bath while 1.5 mL (0.018 mole) of pyridine in 3 mL of dichloromethane was added dropwise. After 1 hr at 0° C., the solution was held at 3° C. in a refrigerator for 48 hr before it was washed with water, then with dilute hydrochloric acid and dried with sodium sulfate. The volatiles were removed to give 3.0 g of oil which was purified by chromatography on Silica gel 40 (dichloromethane as eluent) to give 2.15 g (67%) of bis(2-fluoro-2,2-dinitroethyl)carbonate, pentafluorosulfanylimine; $^1$H-NMR (CDCl$_3$): 5.42 (d); IR (film): 1695 (C=N); 1615 (NO$_2$); 910–790 (SF$_5$).

Anal. Calcd for C$_5$H$_4$F$_7$N$_5$O$_{10}$S: C, 13.07; H, 0.88; F, 28.96; N, 15.25; S, 6.98 Found: C, 13.29; H, 0.87; F, 29.03; N, 14.60; S, 7.18.

A sample of the bis(2-fluoro-2,2-dinitroethyl)carbonate, pentafluorosulfanylimine product in chloroform/dichloromethane/hexanes was cooled in a dry ice-acetone bath to give crystals The solution was decanted from the crystals which were thoroughly dried at approximately $-20°$ C. with a rapid stream of nitrogen The crystals of bis(2-fluoro-2,2-dinitroethyl)carbonate, pentafluorosulfanylimine melted at −4° C. The liquid density of bis(2-fluoro-2 2-dinitroethyl)carbonate, pentafluorosulfanylimine was measured to be 1.82 g/cc (pycnometer). The volatility of bis(2-fluoro-2,2-dinitroethyl)carbonate, pentafluorosulfanylimine was found to be about one-half that of FEFO as measured by thermogravimetric analysis (at 117° C., the rate of weight loss for bis(2-fluoro-2,2-dinitroethyl)carbonate, pentafluorosulfanylimine was 0.0536% per minute compared to 0.1039% per minute for FEFO).

Preparation of Pentafluorosulfanyldichloroimine Starting Material

A method of preparing the pentafluorosulfanyldichloroimine, $SF_5N=Cl_2$, starting material is taught by C. W. Tullock Et al., "Synthesis and Chemistry of $SF_5Cl$," Journal of the American Chemical Society, Vol 86 (1964), pp. 357–61, at page 359, herein incorporated by reference in its entirety.

Tullock et al. first teach the synthesis of $SF_5Cl$:

Synthesis of Sulfur Chloride pentafluoride. Finely divided cesium fluoride (172 g., 1.13 moles), sulfur tetrafluoride (108 g., 1.00 mole), and chlorine (71 g., 1.00 mole) were heated with agitation for 1 hr. at 100°, for 1 hr. at 150°, and for 2 hr. at 175° in a 500-ml. Hastelloy C steel pressure vessel. The volatile product recovered (100 g.) was distilled through a low temperature still (still head cooled to −60° since $SF_5Cl$ freezes at −64°). The colorless fraction distilling at −23 to −23° (lit. [4] reports −21°) amounted to 125 g.; . . . indicated the distillate contained at least 95% $SF_5Cl$. The conversion was about 75% . . . .

Tullock et al. then teach the synthesis of $SF_5N=CCl_2$.

Addition of $SF_5Cl$ to CN-Containing Compounds. -All of the ultraviolet-light catalyzed reactions were carried out in a similar manner. The reactor, either a 12-or 22-l. Pyrex flask was provided with a quartz well, 1.5 in. in diameter and 16 in. deep, which extended from the neck into the center of the flask. A low-pressure mercury vapor resonance lamp, in the form of a tightly wound 10-in quartz spiral, 6 mm. in diameter, which was inserted into the well, was the ultraviolet light source. The lamp was powered by a 5000 v., 60-milliamp transformer. The reactor flask was evacuated behind a protective shield and the gaseous reactants were added in sufficient quantities so that their initial pressure ranged from 600 to 730 mm. pressure. Since the products were liquids, the extent of the reaction could be estimated by the decrease in pressure as reaction proceeded. When reaction stopped or slowed considerably, the reactants were removed and were purified by distillation either through a packed, low-temperature column or a spinning-band column. A. Preparation of $SF_5N=CCl_2$.

- A 12-l., round-bottomed flask containing cyanogen chloride (14 g., 0.23 mole) and $SF_5Cl$ (37 g., 0.23 mole) was irradiated for 6.5 hr., after which the contents were transformed to a liquid nitrogen cooled, evacuated trap and then allowed to warm up gradually to room temperature. The liquid from two such experiments were combined to give 37 g., amounting to a 36% conversion of colorless $SF_5=CCl_2$, b.p. 86–88° . . .

Obviously, numerous modifications and variations of the present invention are possible in light of the foregoing teachings. It is therefore to be understood that within the scope of the appended claims, the invention may be practiced otherwise than as specifically described

What is claimed new and desired to be secured by Letters Patent of the United States is:

1. A compound having the formula $SF_5N=C[OCH_2CF(NO_2)_2]_2$.

* * * * *